United States Patent
Ishihara et al.

(10) Patent No.: US 9,828,318 B2
(45) Date of Patent: Nov. 28, 2017

(54) METHOD FOR PRODUCING GLYCOLS FROM OXIRANE COMPOUNDS

(71) Applicant: Sumitomo Chemical Company, Limited, Tokyo (JP)

(72) Inventors: Shinjiro Ishihara, Ehime (JP); Shoko Ikeda, Chiba (JP); Masayuki Yoshii, Chiba (JP); Makoto Murata, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/362,940

(22) PCT Filed: Dec. 12, 2012

(86) PCT No.: PCT/JP2012/082853
§ 371 (c)(1),
(2) Date: Jun. 5, 2014

(87) PCT Pub. No.: WO2013/089271
PCT Pub. Date: Jun. 20, 2013

(65) Prior Publication Data
US 2014/0378714 A1 Dec. 25, 2014

(30) Foreign Application Priority Data

Dec. 13, 2011 (JP) .................................. 2011-271976
May 10, 2012 (JP) .................................. 2012-108285

(51) Int. Cl.
C07C 41/03 (2006.01)

(52) U.S. Cl.
CPC ............ C07C 41/03 (2013.01); *Y02P 20/582* (2015.11)

(58) Field of Classification Search
CPC ..................................................... C07C 41/03
See application file for complete search history.

(56) References Cited

U.S. PATENT DOCUMENTS

| | | |
|---|---|---|
| 4,551,566 A | 11/1985 | Robson et al. |
| 4,578,524 A | 3/1986 | Keen |
| 4,760,200 A * | 7/1988 | Keen et al. .................... 568/867 |
| 6,147,265 A | 11/2000 | Iwakura et al. |

FOREIGN PATENT DOCUMENTS

| | | |
|---|---|---|
| JP | S56-73035 A | 6/1981 |
| WO | WO 9511213 * | 4/1995 |

OTHER PUBLICATIONS

National Center for Biotechnology Information. PubChem Compound Database, CID=8087, https://pubchem.ncbi.nlm.nih.gov/compound/8087 (accessed Aug. 23, 2015), 31 pages creation date Mar. 26, 2005.*
National Center for Biotechnology Information. PubChem Compound Database, CID=32611, https://pubchem.ncbi.nlm.nih.gov/compound/32611 (accessed Aug. 23, 2015), 29 pages creation date Aug. 8, 2005.*
Tanabe ("Niobic acid as an unusual acidic solid material", Materials Chemistry and Physics, vol. 17, Issues 1-2, Apr.-May 1987, pp. 217-225).*
Kozo Tanabe, "Niobic acid as an unusual acidic solid material", Materials and Physics, vol. 17, Issues 1-2, Apr.-May 1987, pp. 217-225.*
Iizuka et al., "Acidic and Catalytic Properties of Niobium Pentoxide", Bull. Chem. Soc. Jpn., 56, Oct. 1983, pp. 2927-2931.*
Tanabe et al., "New Solid Acids and Bases: Their Catalytic Properties", Technology and Engineering, 1990, pp. 60 and 61.*
Kirk-Othmer Encyclopedia of Chemical Technology, John Wiley & Sons, Inc., pp. 1-10 (2000).
"Shokubai Kagaku (Catalyst Chemistry)," pp. 518-519, 525 (1981).
Dow Dipropylene Glycol LO+ Technical Data Sheet.
Dow Tripropylene Glycol, Acrylate Grade Technical Data Sheet.
Int'l Search Report dated Feb. 5, 2013 in Int'l Application No. PCT/JP2012/082853.

* cited by examiner

*Primary Examiner* — Rosalynd A Keys
(74) *Attorney, Agent, or Firm* — Panitch Schwarze Belisario & Nadel LLP

(57) ABSTRACT

The objective of the present invention is to provide a method for the highly selective production of dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70. The present invention is a method for producing dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70, the method comprising a reaction step of making a reactant comprising propylene oxide and water react in the presence of a catalyst, wherein the catalyst comprises at least one element selected from the group consisting of vanadium, niobium, and tantalum, and the Hammett acidity function (H) of the catalyst satisfies H≤9.3.

5 Claims, No Drawings

METHOD FOR PRODUCING GLYCOLS FROM OXIRANE COMPOUNDS

CROSS-REFERENCE TO RELATED APPLICATION

This application is a Section 371 of International Application No. PCT/JP2012/082853, filed Dec. 12, 2012, which was published in the Japanese language on Jun. 20, 2013, under International Publication No. WO 2013/089271 A1, and the disclosure of which is incorporated herein by reference.

TECHNICAL FIELD

The present invention relates to a method for the highly selective production of dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70.

BACKGROUND ART

Dipropylene glycol is a compound that is used as a raw material for polyester resin or polyurethane resin, a raw material for acrylates, an operating oil, an antifreezing solution, a wetting agent for cellophane, a compatibilizing agent, a solvent for printing ink, a raw material for cosmetics, solvent for perfume, solvent for toiletries, and so on, whereas tripropylene glycol is a compound that is used as a raw material for polyester resin or polyurethane resin, a raw material for acrylates, a solvent for a water-soluble oil, a solvent for ink, and so on. Dipropylene glycol and tripropylene glycol are known to be produced as byproducts when producing propylene glycol.

It is known that dipropylene glycol produced industrially is commonly a mixture of 1,1'-oxybis-2-propanol, 2,2'-oxybis-1-propanol, and 2-(2-hydroxypropoxy)-1-propanol (see, for example, non-patent document 1).

Moreover, it is known that tripropylene glycol produced industrially is commonly a mixture of 1,1'-[(1-methyl-1,2-ethanediyl)bis(oxy)]bis-2-propanol, 2,2'-[(1-methyl-1,2-ethanediyl)bis(oxy)]bis-1-propanol, 2-[1-(2-hydroxypropoxy)-1,2-propoxy]-1-propanol, and 2-[2-(2-hydroxypropoxy)-propoxy]-1-propanol (see, for example, non-patent document 1).

The proportion of 1,1'-oxybis-2-propanol contained in commercially available dipropylene glycol is 0.10 to 0.70, and the proportion of 1,1'-[(1-methyl-1,2-ethanediyl)bis(oxy)]bis-2-propanol contained in commercially available tripropylene glycol is 0.10 to 0.70. Such commercially available dipropylene glycol and tripropylene glycol are known to be produced as byproducts when producing propylene glycol by making propylene oxide react with excessive water in the absence of a catalyst (see, for example, non-patent document 1).

On the other hand, patent document 1, for example, discloses a production method to obtain an alkylene glycol with high selectivity while generating almost no dialkylene glycol or trialkylene glycol by making an alkylene oxide react with water in the presence of carbon dioxide using a compound one or more element selected from the group consisting of titanium, zirconium, vanadium, niobium, tantalum, and chromium as a catalyst.

PRIOR ART DOCUMENT

Patent Document

[Patent Document 1] JP-A-56-073035

Non-Patent Document

[Non-Patent Document 1] Alton E. Martin, "Glycols, Propylene Glycols", Kirk-Othmer Encyclopedia of Chemical Technology, 2000

SUMMARY OF THE INVENTION

Problems to be Solved by the Invention

Patent document 1, however, contains no disclosure about the proportion of 1,1'-oxybis-2-propanol contained in dipropylene glycol and the proportion of 1,1'-[(1-methyl-1,2-ethanediyl)bis(oxy)]bis-2-propanol contained in tripropylene glycol.

The objective of the present invention is to provide a method for the highly selective production of dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70.

Means for Solving the Problems

The present invention relates to a method for producing dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70, the method comprising a reaction step of making a reactant comprising propylene oxide and water react in the presence of a catalyst, wherein the catalyst comprises at least one element selected from the group consisting of vanadium, niobium, and tantalum, and the Hammett acidity function (H) of the catalyst satisfies $H \leq 9.3$.

Effect of the Invention

According to the present invention, it is possible to highly selectively produce dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70.

MODE FOR CARRYING OUT THE INVENTION

In the method of the present invention, while a reactant containing propylene oxide and water is made to react in the presence of a catalyst comprising at least one element selected from the group consisting of vanadium, niobium and tantalum in order to produce dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70, the Hammett acidity function (H) of the catalyst is required to satisfy $H \leq 9.3$.

In the present invention, dipropylene glycol and/or tripropylene glycol can be produced with higher selectivity by using a catalyst which contains at least one element selected from the group consisting of vanadium, niobium and tantalum and the Hammett acidity function (H) of which satisfies H≤9.3 as compared with catalyst-free reaction. Although either a homogeneous catalyst or a heterogeneous catalyst may be adopted as the catalyst to be used in the present invention, a heterogeneous catalyst is preferred from the viewpoint of industrial practices.

In the method of the present invention, the selectivity to dipropylene glycol and tripropylene glycol can be increased by reducing the ratio of water to propylene oxide and/or making the reactant comprising propylene oxide and water further include propylene glycol. The total selectivity to dipropylene glycol and tripropylene glycol is preferably 50% or more, more preferably 60% or more, and even more preferably 70% or more.

In the present invention, the Hammett acidity function (H) of a catalyst is measured with a method using an indicator. The method using an indicator is used commonly for measuring the acidity or the basicity of a solid. (See, for example, non-patent document 2: Tominaga KEII, "Shokubai Kagaku (Catalyst Chemistry)" published by Tokyo Kagaku Dojin Shuppan, 1981, pp. 518-519, 525-526).

The catalyst to be used in the present invention is required to have a Hammett acidity function (H) that satisfies H≤9.3 and has the feature of not coloring even if phenolphthalein is used as an indicator.

The method of using phenolphthalein as an indicator is performed in the following manner.

To 2 to 5 ml of cyclohexane is added 0.25 g of crushed catalyst, followed by being allowed to stand at room temperature for 10 minutes. About 1 ml of a 0.05 mol/l phenolphthalein solution (40 volume % of ethanol and 60 volume % of cyclohexane are used as solvent) is added thereto, followed by being allowed to stand at room temperature for 30 minutes. When the catalyst colors into pink or reddish violet, the Hammett acidity function (H) of the catalyst satisfies H>9.3, whereas when the catalyst fails to color, the Hammett acidity function (H) of the catalyst satisfies H≤9.3.

On the other hand, in the case of a catalyst that is difficult to determine its color development, for example, a black catalyst, it may be impossible to determine color development by a method in which the presence or absence of color development is checked using phenolphthalein as an indicator. In this case, 2 to 5 ml of cyclohexane is added to 0.25 g of crushed catalyst, followed by being allowed to stand at room temperature for 10 minutes. About 1 ml of a 0.05 mol/l phenolphthalein solution (40 volume % of ethanol and 60 volume % of cyclohexane are used as solvent) is added thereto, followed by being allowed to stand at room temperature for 30 minutes. After removal of a supernatant, the catalyst recovered is heated up to 300° C. at a rate of 5° C./minute under nitrogen flow. In measurement of the catalyst recovered with FT-IR or NMR, when a peak derived from phenolphthalein can be confirmed, the Hammett acidity function (H) of the catalyst satisfies H>9.3, whereas when no peak derived from phenolphthalein can be confirmed, the Hammett acidity function (H) of the catalyst satisfies H≤9.3.

While the lower limit of the Hammett acidity function (H) of the catalyst is not particularly limited, the Hammett acidity function (H) of the catalyst preferably satisfies H>−5.6, and it is preferred that the catalyst does not color even if benzalacetophenone is used as an indicator. The method of using benzalacetophenone as an indicator is performed in the following manner.

To 2 to 5 ml of cyclohexane is added 0.25 g of crushed catalyst, followed by being allowed to stand at room temperature for 10 minutes. About 1 ml of a 0.05 mol/L benzalacetophenone solution (cyclohexane is used as solvent) is added thereto and then allowed to stand at room temperature for 30 minutes. When the catalyst colors into yellow, the Hammett acidity function (H) of the catalyst satisfies H≤−5.6, whereas when the catalyst fails to color, the Hammett acidity function (H) of the catalyst satisfies H>−5.6.

On the other hand, in the case of a catalyst that is difficult to determine its color development, for example, a black catalyst, it may be impossible to determine color development by a method in which the presence or absence of color development is checked using benzalacetophenone as an indicator. In this case, 2 to 5 ml of cyclohexane is added to 0.25 g of crushed catalyst, followed by being allowed to stand at room temperature for 10 minutes. About 1 ml of a 0.05 mol/L benzalacetophenone solution (cyclohexane is used as solvent) is added thereto and then allowed to stand at room temperature for 30 minutes. After removal of a supernatant, the catalyst recovered is heated up to 300° C. at a rate of 5° C./minute under nitrogen flow. In measurement of the catalyst recovered with FT-IR or NMR, when a peak derived from benzalacetophenone can be confirmed, the Hammett acidity function (H) of the catalyst satisfies H≤−5.6, whereas when no peak derived from benzalacetophenone can be confirmed, the Hammett acidity function (H) of the catalyst satisfies H>−5.6.

In the present invention, the proportion of 1,1'-oxybis-2-propanol contained in dipropylene glycol and the proportion of 1,1'-[(1-methyl-1,2-ethanediyl)bis(oxy)]bis-2-propanol contained in tripropylene glycol can be calculated using the following formulae.

Proportion of 1,1'-oxybis-2-propanol=(content of 1,1'-oxybis-2-propanol)/{(content of 1,1'-oxybis-2-propanol)+(content of 2,2'-oxybis-1-propanol)+(content of 2-(2-hydroxypropoxy)-1-propanol)}

Proportion of 1,1'-[(1-methyl-1,2-ethanediyl)bis(oxy)]bis-2-propanol=(content of 1,1'-[(1-methyl-1,2-ethanediyl)bis(oxy)]bis-2-propanol)/{(content of 1,1'-[(1-methyl-1,2-ethanediyl)bis(oxy)]bis-2-propanol)+(content of 2,2'-[(1-methyl-1,2-ethanediyl)bis(oxy)]bis-1-propanol)+(content of 2-[1-(2-hydroxypropoxy)-2-propoxy]-1-propanol)+(content of 2-[2-(2-hydroxypropoxy)-propoxy]-1-propanol)}

In the method of the present invention, the propylene oxide to be used as a reactant may be propylene oxide produced by any production method and examples thereof include propylene oxide produced by dehydrochlorinating, with a basic compound, a mixture produced by making propylene react with an aqueous solution of chlorine, propylene oxide produced by making propylene react in the presence of a catalyst with ethylbenzene hydroperoxide produced by oxidizing ethylbenzene, propylene oxide produced by making propylene react in the presence of a catalyst with isopropylbenzene hydroperoxide produced by oxidizing isopropylbenzene, propylene oxide produced by making propylene react in the presence of a catalyst with tert-butyl hydroperoxide produced by oxidizing isobutane, and propylene oxide produced by making propylene react in the presence of a catalyst with hydrogen peroxide.

In the method of the present invention, the water to be used as a reactant is not particularly limited and examples thereof include distilled water, pure water, ion exchange water, and steam condensate.

Examples of the catalyst to be used for the method of the present invention which contains at least one element selected from the group consisting of vanadium, niobium and tantalum and the Hammett acidity function (H) of which satisfies H≤9.3 include an oxide, a sulfide, an acid, a halide, a phosphorus compound or a polyacid of at least one element selected from the group consisting of vanadium, niobium and tantalum. An oxide or an acid containing at least one element selected from the group consisting of vanadium, niobium and tantalum is preferred because it will afford dipropylene glycol and/or tripropylene glycol with high selectivity. A catalyst containing at least one element selected from the group consisting of niobium and tantalum is preferred and a catalyst containing niobium is particularly preferred.

Examples of the oxide containing at least one element selected from the group consisting of vanadium, niobium and tantalum include vanadium pentoxide, vanadium dioxide, vanadium trioxide, niobium pentoxide, niobium dioxide, niobium monoxide and tantalum pentoxide and examples of the acid containing at least one element selected from the group consisting of vanadium, niobium and tantalum include vanadic acid, niobic acid and tantalic acid.

In the method of the present invention, the catalyst containing at least one element selected from the group consisting of vanadium, niobium and tantalum is required to have a Hammett acidity function (H) satisfying H≤9.3.

If the Hammett acidity function (H) of the catalyst gets H>9.3, the proportion of 1,1'-oxybis-2-propanol contained in dipropylene glycol becomes greater than 0.70 and the proportion of 1,1'-[(1-methyl-1,2-ethanediyl)bis(oxy)]bis-2-propanol contained in tripropylene glycol becomes greater than 0.70.

In the method of the present invention, the proportion of 1,1'-oxybis-2-propanol contained in dipropylene glycol is 0.10 to 0.70. The proportion is preferably 0.15 to 0.60, more preferably 0.20 to 0.50. The proportion of 1,1'-[(1-methyl-1,2-ethanediyl)bis(oxy)]bis-2-propanol contained in tripropylene glycol is 0.10 to 0.70. The proportion is preferably 0.15 to 0.60, more preferably 0.20 to 0.50.

In the method of the present invention, a catalyst which contains at least one element selected from the group consisting of vanadium, niobium and tantalum and the Hammett acidity function (H) of which satisfies H≤9.3 may be used alone or in combination of two or more.

In the method of the present invention, it is also permitted to co-localize a catalyst which contains at least one element selected from the group consisting of vanadium, niobium and tantalum and the Hammett acidity function (H) of which is H≤9.3 with a catalyst other than the catalyst stipulated in the present invention as long as dipropylene glycol in which the proportion of 1,1'-oxybis-2-propanol is 0.10 to 0.70 and/or tripropylene glycol in which the proportion of 1,1'-[(1-methyl-1,2-ethanediyl)bis(oxy)]bis-2-propanol is 0.10 to 0.70 are produced. Examples of the catalyst other than the catalyst stipulated in the present invention include silica, alumina, silica-alumina, zeolite, titania, zirconia, ceria, activated carbon, graphite, magnesia and calcia.

Preferably, the catalyst to be used for the present invention is crystallized in the presence of supercritical water. Supercritical water is water with temperature and pressure higher than the temperature and the pressure at the critical point. Water is not particularly limited and examples thereof include distilled water, pure water, ion exchange water, and steam condensate.

Preferably, the catalyst crystallized in the presence of supercritical water is calcined. Preferable temperature for calcining the catalyst is 50 to 650° C., more preferably 100 to 500° C., even more preferably 200 to 400° C.

The catalyst to be used for the present invention contains at least one element selected from the group consisting of vanadium, niobium and tantalum and also contains an alkali metal and/or an alkaline earth metal. The ratio of the total number of moles of the alkali metal and the alkaline earth metal contained in the catalyst to the total number of moles of the vanadium, the niobium and the tantalum contained in the catalyst is preferably 0.5/1 or less, more preferably 0.05/1 or less, even more preferably 0.005/1 or less. The concentration of the alkali metal and the alkaline earth metal contained in a catalyst and the concentration of the vanadium, the niobium and the tantalum contained in the catalyst can be measured by analyzing by inductively coupled plasma spectrometry a sample prepared by dry ashing the catalyst and dissolving it in an acid.

The ratio of the total number of moles of alkali metal and alkaline earth metal to the number of moles of vanadium, niobium and tantalum is calculated in the following manner.

The ratio of the total number of moles of alkali metal and alkaline earth metal to the total number of moles of vanadium, niobium and tantalum=(the sum total of the number of moles of alkali metal and alkaline earth metal contained in a catalyst)/(the sum total of the number of moles of vanadium, niobium and tantalum contained in the catalyst)

In the present invention, the alkali metal may be Li, Na, K, Rb or Cs and the alkaline earth metal may be Be, Mg, Ca, Sr or Ba.

In the present invention, the catalyst which contains at least one element selected from the group consisting of vanadium, niobium and tantalum and the Hammett acidity function (H) of which satisfies H≤9.3 may or may not have a peak that indicates a spacing d in X-ray diffraction. As used herein, the peak that indicates a spacing d in X-ray diffraction is a peak derived from crystallinity or regularity possessed by solid.

Examples of the method for synthesizing a catalyst having a peak that indicates a spacing d include a method in which niobic acid having no peak that indicates a spacing d is brought into contact with supercritical water and thereby converted into niobium pentoxide having a peak that indicates a spacing d and a method in which niobic acid is calcined into niobium pentoxide. The calcination time is usually 0.1 to 30 hours, preferably 0.5 to 20 hours. The calcination temperature is usually 450 to 1000° C., preferably 500 to 800° C.

The measurement of X-ray diffraction is carried out, for example, by using an X-ray diffraction apparatus MiniFlexII (manufactured by Rigaku Corporation); specifically, a catalyst is placed on a sample plate and mounted on the sample stage of the X-ray diffraction apparatus MiniFlexII and then the measurement is carried out under the following conditions.

Light source: Cukα (Counter monochromator was used for removal of Kβ)
Divergence slit: 0.625°
Receiving slit: 0.3 mm
Scattering slit: 1.25°
Voltage: 30 kV
Current: 15 mA.
Sampling width: 0.02°
Scan speed: 0.02°/second The reaction temperature applied in the present invention is usually 30 to 350° C., preferably 50 to 300° C.

The reaction pressure applied in the present invention is usually normal pressure to 50 MPa-G, preferably 0.1 to 20 MPa-G.

The reaction mode applied in the present invention may be any mode. For example, a reaction operation may be any of a batch method, a semibatch method or a continuous method, and a reactor may be a single-stage or multi-stage vessel type reactor or a tubular reactor composed of a single tube or multiple tubes arranged in parallel. Examples of the method of controlling the reaction temperature include an external heat exchange system, a self heat exchange system, and a heat insulation system.

In the present invention, the molar ratio of water to propylene oxide contained in the reactant is 0.05/1 to 100/1, preferably 0.1/1 to 50/1, more preferably 0.2/1 to 10/1. In order to increase the yield of dipropylene glycol and/or tripropylene glycol, propylene glycol is preferably contained in the reactant. While the propylene glycol contained in the reactant may be propylene glycol produced by any production method, one resulting from the reaction of the present invention and one resulting from the purification of the reactant are particularly preferred. In order to increase the yield of tripropylene glycol, dipropylene glycol may be contained in the reactant. While the dipropylene glycol contained in the reactant may be dipropylene glycol produced by any production method, one resulting from a reaction and one resulting from the purification of the reactant are particularly preferred.

In the present invention, when water remains unreacted in dipropylene glycol and/or tripropylene glycol resulting from the reaction between propylene oxide and water, the unreacted water can be recycled to the reactor and used again as part of the reactant. Moreover, when propylene oxide remains unreacted in dipropylene glycol and/or tripropylene glycol resulting from the reaction between propylene oxide and water, the unreacted propylene oxide can be recycled to the reactor and used again as part of the reactant.

In the reaction of the present invention, propylene glycol may be formed and at least part of the propylene glycol formed may be purified and recovered as a product.

In the present invention, a recovery step of separating dipropylene glycol and/or tripropylene glycol from the reaction mixture may be provided after the reaction step. Examples of the method for the recovery of dipropylene glycol and/or tripropylene glycol include distillation, partial condensation and extraction. Dipropylene glycol and/or tripropylene glycol may be recovered as a mixture of both the compounds and also may be separated from each other and then recovered. When distillation is used for the recovery method, the temperature of the distillation column is usually 0 to 300° C., preferably 10 to 250° C., the pressure is usually −0.1 to 20 MPa-G, preferably −0.09 to 10 MPa-G, and the number of plates is usually 1 to 100, preferably 10 to 30 though these are not limited particularly thereto.

Reference Example 1

Gas chromatographic analysis of commercially available dipropylene glycols revealed that the proportion of 1,1'-oxybis-2-propanol contained in dipropylene glycol was 0.31 in the product available from Kanto Chemical Co., Inc., 0.46 in the product available from Tokyo Chemical Industry Co., Ltd., 0.35 in the product available from Aldrich, and 0.33 in the product available from Wako Pure Chemical Industries, Ltd.

Reference Example 2

Gas chromatographic analysis of commercially available tripropylene glycols revealed that the proportion of 1,1'-[(1-methyl-1,2-ethanediyl)bis(oxy)]bis-2-propanol contained in tripropylene glycol was 0.31 in the product available from Wako Pure Chemical Industries, Ltd., 0.32 in the product available from Tokyo Chemical Industry Co., Ltd., 0.20 in the product available from Aldrich, and 0.27 in the product available from Alfa Aesar.

EXAMPLES

The present invention is described below with reference to Examples.

The conversions and the selectivities in Examples using propylene oxide and water as reactants were calculated by (Formula A), (Formula B) and (Formula C) given below.

Conversion of propylene oxide=(the number of moles of propylene oxide consumed)/(the number of moles of propylene oxide charged)×100 (%) (Formula A)

Selectivity to dipropylene glycol=(the number of moles of dipropylene glycol generated)×2/(the number of moles of propylene oxide consumed)×100(%) (Formula B)

Selectivity to tripropylene glycol=(the number of moles of tripropylene glycol generated)×3/(the number of moles of propylene oxide consumed)×100(%) (Formula C)

The conversions and the selectivities in Examples using propylene oxide, water and propylene glycol as reactants were calculated by (Formula D), (Formula E), (Formula F) and (Formula (G) given below. When the conversion of propylene glycol was calculated using (Formula E) to be minus, selectivities were calculated using (Formula B) and (Formula C) because propylene glycol was generated in the system.

Conversion of propylene oxide=(the number of moles of propylene oxide consumed)/(the number of moles of propylene oxide charged)×100 (%) (Formula D)

Conversion of propylene glycol=(the number of moles of propylene glycol consumed)/(the number of moles of propylene glycol charged)×100 (%) (Formula E)

Selectivity to dipropylene glycol=[(the number of moles of dipropylene glycol generated)×2/{(the number of moles of propylene oxide consumed)+(the number of moles of propylene glycol consumed)}]×100(%) (Formula F)

Selectivity to tripropylene glycol=[(the number of moles of tripropylene glycol generated)×3/{(the number of moles of propylene oxide consumed)+(the number of moles of propylene glycol consumed)}]×100(%) (Formula G)

In the present invention, the total number of moles of vanadium, niobium and tantalum contained in a catalyst was calculated assuming that vanadium, niobium and tantalum each is present in the form of $X_2O_5$ (X denotes vanadium, niobium or tantalum) regardless of the presence or absence of inclusion of alkali metal and/or alkaline earth metal.

Example 1

(1) Preparation of Catalyst 90 g of ion exchange water was added to 10 of niobic acid and then stirred for 3 hours. While performing filtration, the residue was washed with 1 L of ion exchange water and then dried at 60° C. for 18 hours, affording water-washed niobic acid. 0.36 g of the resulting water-washed niobic acid and 1.8 g of ion exchange water were mixed together and then placed and sealed into a reaction vessel made of HASTEL-LOY having a capacity of 5 ml. Then, crystals were formed in the presence of supercritical water by heating was applied at 400° C. for 10 minutes under shaking. Thus, a solid was obtained. The solid was dried with an evaporator, affording niobium oxide (A).

(2) Analysis of Catalyst

X-ray diffraction of niobium oxide (A) was measured by using an X-ray diffraction apparatus and thereby was confirmed to have a peak that indicates a spacing d.

In order to measure the Hammett acidity function (H) of niobium oxide (A), 5 ml of cyclohexane was added to 0.25 g of niobium oxide (A) and then allowed to stand at room temperature for 10 minutes. About 1 ml of a 0.05 mol/l phenolphthalein solution (40 volume % of ethanol and 60 volume % of cyclohexane were used as solvent) was added thereto and then was allowed to stand at room temperature for 30 minutes. Thus, the catalyst was not colored by phenolphthalein, that is, the Hammett acidity function (H) satisfied H≤9.3.

To a mixture prepared by adding 5 ml of cyclohexane to 0.25 g of niobium oxide (A) and then allowing to stand at room temperature for 10 minutes was added about 1 ml of a 0.05 mol/l benzalacetophenone solution (cyclohexane was used as solvent), followed by being allowed to stand at room temperature for 30 minutes. Thus, the catalyst was not colored by benzalacetophenone, that is, the Hammett acidity function (H) satisfied H>−5.6.

Niobium oxide (A) was dry ashed and dissolved in an acid, and then the concentration of alkali metal and alkaline earth metal contained in niobium oxide (A) was measured by inductively coupled plasma spectrometry to be 0.022% by weight (Na=0.003% by weight, K=0.006% by weight, Mg=0.008% by weight, Ca=0.005% by weight, others were not detected). Thus, the ratio of the total number of moles of alkali metal and alkaline earth metal to the number of moles of niobium was 0.0006.

(3) Evaluation of Reaction

Into an autoclave were introduced 57 g of propylene oxide, 9 g of water, 75 g of propylene glycol and 1.0 g of niobium oxide (A) obtained by repeating the operations disclosed in Example 1 (1), and then the inside of the autoclave was purged fully with nitrogen gas. Heat was applied so as to adjust the temperature within the autoclave to 180° C. and reaction was performed for 120 minutes under stirring, affording a reaction solution. Gas chromatographic analysis of the reaction solution revealed that the conversion of propylene oxide was 87%, the conversion of propylene glycol was 25%, the selectivity to dipropylene glycol was 62%, the selectivity to tripropylene glycol was 28%, the proportion of 1,1'-oxybis-2-propanol contained in dipropylene glycol was 0.32, and the proportion of 1,1'-[(1-methyl-1,2-ethanediyl)bis(oxy)]bis-2-propanol contained in tripropylene glycol was 0.32.

Example 2

(1) Preparation of Catalyst

Niobium oxide (B) was obtained by repeating the operations described in Example 1(1) and calcining the resulting niobium oxide (A) at 300° C. for 3 hours under air flow.

(2) Analysis of Catalyst

X-ray diffraction of niobium oxide (B) was measured by using an X-ray diffraction apparatus and thereby was confirmed to have a peak that indicates a spacing d.

Measurement of the Hammett acidity function by the method described in Example 1 (2) revealed that niobium oxide (B) failed to be colored by phenolphthalein, that is, H≤9.3, and failed to be colored by benzalacetophenone, that is, H>−5.6.

The concentration of alkali metal and alkaline earth metal in niobium oxide (B) was measured to be 0.011% by weight (Na=0.003% by weight, K=0.005% by weight, Mg=0.0006% by weight, Ca=0.002% by weight, others were not detected). Thus, the ratio of the total number of moles of alkali metal and alkaline earth metal to the number of moles of niobium was 0.0007.

(3) Evaluation of Reaction

To an autoclave were introduced 130 g of propylene oxide, 20 g of water and 1.0 g of niobium oxide (B), followed by fully purging the inside of the autoclave with nitrogen gas. Heat was applied so as to adjust the temperature within the autoclave to 180° C. and reaction was performed for 360 minutes under stirring, affording a reaction solution. Gas chromatographic analysis of the reaction solution revealed that the conversion of propylene oxide was 98%, the selectivity to dipropylene glycol was 37%, the selectivity to tripropylene glycol was 25%, the proportion of 1,1'-oxybis-2-propanol contained in dipropylene glycol was 0.29, and the proportion of 1,1'-[(1-methyl-1,2-ethanediyl)bis(oxy)]bis-2-propanol contained in tripropylene glycol was 0.26.

Example 3

(3) Evaluation of Reaction

Reaction was carried out by the same method as described in Example 1(3) except that niobium oxide (D) obtained by the method described in Example 2(1) was used instead of niobium oxide (A). Then, it was revealed that the conversion of propylene oxide was 99%, the conversion of propylene glycol was 29%, the selectivity to dipropylene glycol was 54%, the selectivity to tripropylene glycol was 35%, the proportion of 1,1'-oxybis-2-propanol contained in dipropylene glycol was 0.26, and the proportion of 1,1'-[(1-methyl-1,2-ethanediyl)bis(oxy)]bis-2-propanol contained in tripropylene glycol was 0.23.

Example 4

(1) Preparation of Catalyst

The operation of adding 200 ml of distilled water to 30 g of niobic acid, followed by stirring and subsequent filtration was repeated three times. The resulting niobic acid was dried at 10 Torr and 70° C. for 3 hours in a vacuum dryer. To 6.3 g of the dried niobic acid were added 0.1 g of sodium hydroxide and 150 g of water, and then water was removed using an evaporator, followed by calcination at 600° C. for 3 hours. The operation of adding 200 ml of distilled water to that calcined solid, followed by stirring and subsequent filtration was repeated three times. The resulting solid was dried at 10 Torr and 70° C. for 3 hours in a vacuum dryer, affording niobium oxide (C).

(2) Analysis of Catalyst

X-ray diffraction of niobium oxide (C) was measured by using an X-ray diffraction apparatus and thereby was confirmed to have a peak that indicates a spacing d.

Measurement of the Hammett acidity function (H) by the method described in Example 1(2) revealed that niobium oxide (C) failed to be colored by phenolphthalein, that is, H≤9.3, and failed to be colored by benzalacetophenone, that is, H>−5.6.

The concentration of alkali metal and alkaline earth metal in niobium oxide (C) was measured to be 0.86% by weight (Na=0.84% by weight, K=0.02% by weight, others were not detected). Thus, the ratio of the total number of moles of alkali metal and alkaline earth metal to the number of moles of niobium was 0.049.

(3) Evaluation of Reaction

Reaction was carried out by the same method as described in Example 2(3) except that 3.0 g of niobium oxide (C) was used instead of 1.0 g of niobium oxide (B). Then, it was revealed that the conversion of propylene oxide was 88%, the selectivity to dipropylene glycol was 53%, the selectivity to tripropylene glycol was 22%, the proportion of 1,1'-oxybis-2-propanol contained in dipropylene glycol was 0.46, and the proportion of 1,1'-[(1-methyl-1,2-ethanediyl)bis(oxy)]bis-2-propanol contained in tripropylene glycol was 0.43.

Example 5

(1) Preparation of Catalyst

The operation of adding 200 ml of distilled water to 30 g of niobic acid, followed by stirring and subsequent filtration was repeated three times. The resulting solid was dried at 10 Torr and 70° C. for 3 hours in a vacuum dryer. To 6.3 g of the dried niobic acid were added 24 g of a 1 mol/l aqueous solution of sodium hydroxide and 50 g of water, and then water was removed using an evaporator, followed by calcination of the resulting solid at 600° C. for 3 hours. The operation of adding 200 ml of distilled water to that calcined solid, followed by stirring and subsequent filtration was repeated three times. The solid was dried at 10 Torr and 70° C. for 3 hours in a vacuum dryer, affording niobium oxide (D).

(2) Analysis of Catalyst

Measurement of the Hammett acidity function by the method described in Example 1(2) revealed that niobium oxide (D) failed to be colored by phenolphthalein, that is, H≤9.3, and failed to be colored by benzalacetophenone, that is, H>−5.6.

The concentration of alkali metal and alkaline earth metal in niobium oxide (D) was measured to be 7.26% by weight (Na=7.23% by weight, K=0.03% by weight, others were not detected). Thus, the ratio of the total number of moles of alkali metal and alkaline earth metal to the number of moles of niobium was 0.45.

(3) Evaluation of Reaction

Reaction was carried out by the same method as described in Example 2(3) except that 3.0 g of niobium oxide (D) was used instead of 1.0 g of niobium oxide (B). Then, it was revealed that the conversion of propylene oxide was 93%, the selectivity to dipropylene glycol was 63%, the selectivity to tripropylene glycol was 22%, the proportion of 1,1'-oxybis-2-propanol contained in dipropylene glycol was 0.35, and the proportion of 1,1'-[(1-methyl-1,2-ethanediyl)bis(oxy)]bis-2-propanol contained in tripropylene glycol was 0.38.

Example 6

(2) Analysis of catalyst

X-ray diffraction of niobic acid (E) was measured by using an X-ray diffraction apparatus and thereby was confirmed to have no peak that indicates a spacing d.

Measurement of the Hammett acidity function by the method described in Example 1 (2) revealed that niobic acid (E) failed to be colored by phenolphthalein, that is, H≤9.3, and failed to be colored by benzalacetophenone, that is, H>−5.6.

The concentration of alkali metal and alkaline earth metal in niobic acid (E) was measured to be 0.018% by weight (Na=0.007% by weight, K=0.008% by weight, Mg=0.001% by weight, Ca=0.002% by weight, others were not detected). Thus, the ratio of the total number of moles of alkali metal and alkaline earth metal to the number of moles of niobium was 0.0008.

(3) Evaluation of Reaction

To an autoclave were introduced 130 g of propylene oxide, 20 g of water and 1.3 g of niobic acid (E), followed by fully purging the inside of the autoclave with nitrogen gas. Heat was applied so as to adjust the liquid temperature within the autoclave to 120° C. and reaction was performed for 240 minutes under stirring, affording a reaction solution. Gas chromatographic analysis of the reaction solution revealed that the conversion of propylene oxide was 85%, the selectivity to dipropylene glycol was 62%, the selectivity to tripropylene glycol was 13%, the proportion of 1,1'-oxybis-2-propanol contained in dipropylene glycol was 0.37, and the proportion of 1,1'-[(1-methyl-1,2-ethanediyl)bis(oxy)]bis-2-propanol contained in tripropylene glycol was 0.28.

Example 7

(1) Preparation of Catalyst

Niobium oxide (F) was obtained by calcining the niobic acid (E) described in Example 6 at 600° C. for 2 hours under air flow.

(2) Analysis of Catalyst

X-ray diffraction of niobium oxide (F) was measured by using an X-ray diffraction apparatus and thereby was confirmed to have a peak that indicates a spacing d.

Measurement of the Hammett acidity function by the method described in Example 1 (2) revealed that niobium oxide (F) failed to be colored by phenolphthalein, that is, H≤9.3, and failed to be colored by benzalacetophenone, that is, H>−5.6.

The concentration of alkali metal and alkaline earth metal in niobium oxide (F) was measured to be 0.011% by weight (Na=0.001% by weight, K=0.008% by weight, Ca=0.002% by weight, others were not detected). Thus, the ratio of the total number of moles of alkali metal and alkaline earth metal to the number of moles of niobium was 0.0004.

(3) Evaluation of reaction

Reaction was carried out by the same method as described in Example 2 (3) except that 10.0 g of niobium oxide (F) was used instead of 1.0 g of niobium oxide (B). Then, it was revealed that the conversion of propylene oxide was 100%, the selectivity to dipropylene glycol was 66%, the selectivity to tripropylene glycol was 23%, the proportion of 1,1'-oxybis-2-propanol contained in dipropylene glycol was 0.45, and the proportion of 1,1'-[(1-methyl-1,2-ethanediyl)bis(oxy)]bis-2-propanol contained in tripropylene glycol was 0.31.

Example 8

(3) Evaluation of Reaction

To an autoclave were introduced 118 g of propylene oxide, 37 g of water and 10.0 g of the niobium oxide (F) obtained in Example 7, followed by fully purging the inside of the autoclave with nitrogen gas. Heat was applied so as to adjust the liquid temperature within the autoclave to 120°

C. and reaction was performed for 360 minutes under stirring, affording a reaction solution. Gas chromatographic analysis of the reaction solution revealed that the conversion of propylene oxide was 81%, the selectivity to dipropylene glycol was 52%, the selectivity to tripropylene glycol was 10%, the proportion of 1,1'-oxybis-2-propanol contained in dipropylene glycol was 0.45, and the proportion of 1,1'-[(1-methyl-1,2-ethanediyl)bis(oxy)]bis-2-propanol contained in tripropylene glycol was 0.35.

Example 9

(1) Preparation of Catalyst

Niobium oxide (G) was obtained by calcining niobic acid at 590° C. under air flow.

(2) Analysis of Catalyst

X-ray diffraction of niobium oxide (G) was measured by using an X-ray diffraction apparatus and thereby was confirmed to have a peak that indicates a spacing d.

Measurement of the Hammett acidity function by the method described in Example 1(2) revealed that niobium oxide (G) failed to be colored by phenolphthalein, that is, H≤9.3, and failed to be colored by benzalacetophenone, that is, H>−5.6.

(3) Evaluation of Reaction

Reaction was carried out by the same method as described in Example 1(3) except that 5.0 g of niobium oxide (G) was used instead of 1.0 g of niobium oxide (A). Then, it was revealed that the conversion of propylene oxide was 92%, the conversion of propylene glycol was 30%, the selectivity to dipropylene glycol was 77%, the selectivity to tripropylene glycol was 22%, the proportion of 1,1'-oxybis-2-propanol contained in dipropylene glycol was 0.42, and the proportion of 1,1'-[(1-methyl-1,2-ethanediyl)bis(oxy)]bis-2-propanol contained in tripropylene glycol was 0.41.

Example 10

(1) Preparation of Catalyst

Tantalic acid (I) was obtained by calcining tantalic acid at 250° C. for 2 hours under air flow.

(2) Analysis of Catalyst

X-ray diffraction of tantalic acid (I) was measured by using an X-ray diffraction apparatus and thereby was confirmed to have no peak that indicates a spacing d.

Measurement of the Hammett acidity function by the method described in Example 1 (2) revealed that tantalic acid (I) failed to be colored by phenolphthalein, that is, H≤9.3, and failed to be colored by benzalacetophenone, that is, H>−5.6.

(3) Evaluation of Reaction

Reaction was carried out by the same method as described in Example 2 (3) except that the tantalic acid (I) obtained in Example 11 was used instead of niobium oxide (B). Then, it was revealed that the conversion of propylene oxide was 100%, the selectivity to dipropylene glycol was 74%, the selectivity to tripropylene glycol was 16%, the proportion of 1,1'-oxybis-2-propanol contained in dipropylene glycol was 0.41, and the proportion of 1,1'-[(1-methyl-1,2-ethanediyl)bis(oxy)]bis-2-propanol contained in tripropylene glycol was 0.38.

Comparative Example 1

(1) Preparation of Catalyst

The potassium niobate (J) used was a product available from STREM CHEMICAL.

(2) Analysis of catalyst

Measurement of the Hammett acidity function by the method described in Example 1(2) revealed that potassium niobate (J) colored into pink, that is, H>9.3.

The concentration of alkali metal and alkaline earth metal in potassium niobate (J) was measured to be 17% by weight (K=17% by weight, others were not detected). Thus, the ratio of the total number of moles of alkali metal and alkaline earth metal to the number of moles of niobium was 0.69.

(3) Evaluation of Reaction

Reaction was carried out by the same method as described in Example 2(3) except that 1.3 g of potassium niobate (J) was introduced instead of 1.0 g of niobium oxide (B). Then, it was revealed that the conversion of propylene oxide was 100%, the selectivity to dipropylene glycol was 26%, the selectivity to tripropylene glycol was 37%, the proportion of 1,1'-oxybis-2-propanol contained in dipropylene glycol was 0.83, and the proportion of 1,1'-[(1-methyl-1,2-ethanediyl)bis(oxy)]bis-2-propanol contained in tripropylene glycol was 0.86.

Comparative Example 2

(1) Preparation of Catalyst

The operation of adding 200 ml of distilled water to 30 g of niobic acid, followed by stirring and subsequent filtration was repeated three times. The solid was dried at 10 Torr and 70° C. for 3 hours in a vacuum dryer. 1.52 g of sodium hydroxide and 115 g of water were added to 6.25 g of that resulting niobic acid and then placed and sealed into a reaction vessel made of Teflon having a capacity of 200 ml. Heat was then applied at 175° C. for 40 hours under shaking. The resulting solid was collected by filtration, and the solid collected and 200 ml of distilled water were added to a beaker, stirred for 30 minutes, and then filtered. The solid collected by filtration was calcined at 200° C. for 3 hours in the presence of air, affording niobium oxide (K).

(2) Analysis of Catalyst

X-ray diffraction of niobium oxide (K) was measured by using an X-ray diffraction apparatus and thereby was confirmed to have a peak that indicates a spacing d.

Measurement of the Hammett acidity function by the method described in Example 1(2) revealed that niobium oxide (K) colored into pink, that is, H>9.3.

(3) Evaluation of Reaction

Reaction was carried out by the same method as described in Example 2(3) except that 3.0 g of niobium oxide (K) was introduced instead of 1.0 g of niobium oxide (B). Then, it was revealed that the conversion of propylene oxide was 97%, the selectivity to dipropylene glycol was 42%, the selectivity to tripropylene glycol was 28%, the proportion of 1,1'-oxybis-2-propanol contained in dipropylene glycol was 0.75, and the proportion of 1,1'-[(1-methyl-1,2-ethanediyl)bis(oxy)]bis-2-propanol contained in tripropylene glycol was 0.81.

INDUSTRIAL APPLICABILITY

According to the present invention, it is possible to highly selectively produce dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70.

The invention claimed is:

1. A method for selectively producing dipropylene glycol containing 1,1'-oxybis-2-propanol in a proportion of 0.10 to 0.70 and/or tripropylene glycol containing 1,1'-[(1-methyl-1,2-ethanediyl)bis(oxy)]bis-2-propanol in a proportion of 0.10 to 0.70, the method comprising reacting a reactant comprising propylene oxide with water in the presence of a catalyst, wherein the catalyst is an oxide of at least one element selected from niobium and tantalum, or an acid containing tantalum, wherein the Hammett acidity function (H) of the catalyst satisfies H≤9.3, and wherein the catalyst comprises an alkali metal and/or an alkaline earth metal and optionally further comprises vanadium, and wherein the ratio of the total number of moles of the alkali metal and the alkaline earth metal contained in the catalyst to a total number of moles of vanadium, niobium, and tantalum contained in the catalyst is 0.45 or less.

2. The method according to claim 1, wherein the reactant further comprises propylene glycol.

3. The method according to claim 1, wherein no acid of niobium is contained in the catalyst.

4. The method according to claim 1, wherein the catalyst is selected from the group consisting of niobium dioxide, niobium monoxide, niobium pentoxide, tantalum pentoxide, and tantalic acid.

5. The method according to claim 1, wherein the catalyst is a heterogeneous catalyst.

* * * * *